United States Patent
Locke et al.

(10) Patent No.: US 10,716,711 B2
(45) Date of Patent: *Jul. 21, 2020

(54) TISSUE TREATMENT SYSTEMS AND METHODS HAVING A POROUS SUBSTRATE WITH A COMPRESSED REGION AND AN EXPANDED REGION

(71) Applicant: KCI Licensing, Inc., San Antonio, TX (US)

(72) Inventors: Christopher Brian Locke, Bournemouth (GB); Timothy Mark Robinson, Shillingstone (GB)

(73) Assignee: KCI Licensing, Inc., San Antonio, TX (US)

( * ) Notice: Subject to any disclaimer, the term of this patent is extended or adjusted under 35 U.S.C. 154(b) by 636 days.

This patent is subject to a terminal disclaimer.

(21) Appl. No.: 15/488,156

(22) Filed: Apr. 14, 2017

(65) Prior Publication Data

US 2017/0216100 A1    Aug. 3, 2017

Related U.S. Application Data

(62) Division of application No. 13/678,459, filed on Nov. 15, 2012, now Pat. No. 9,655,807.

(Continued)

(51) Int. Cl.
     *A61F 13/00*        (2006.01)
     *A61L 15/42*        (2006.01)
     (Continued)

(52) U.S. Cl.
     CPC .. *A61F 13/00008* (2013.01); *A61F 13/00029* (2013.01); *A61F 13/00068* (2013.01);
     (Continued)

(58) Field of Classification Search
     CPC .......... A61F 13/00008; A61F 13/00068; A61F 13/00029; A61F 2013/00314;
     (Continued)

(56) References Cited

U.S. PATENT DOCUMENTS 1,355,846 A    10/1920   Rannells
2,547,758 A     4/1951   Keeling
(Continued)

FOREIGN PATENT DOCUMENTS

AU           550575 B2    3/1986
AU           745271 B2    3/2002
(Continued)

OTHER PUBLICATIONS

International Search Report and Written Opinion for corresponding PCT/US2012/065342, dated Feb. 5, 2013.
(Continued)

*Primary Examiner* — Quang D Thanh

(57) ABSTRACT

A system for treating a tissue site of a patient includes a dressing filler adapted to be positioned at the tissue site. The dressing filler includes a porous substrate having at least one compressed region and at least one expanded region. The compressed region of the porous substrate is held in a compressed state by a first coating capable of dissolving in the presence of a fluid, and the expanded region of the porous substrate is held in an expanded state by a second coating.

34 Claims, 8 Drawing Sheets

Related U.S. Application Data

(60) Provisional application No. 61/561,631, filed on Nov. 18, 2011.

(51) Int. Cl.
| | |
|---|---|
| *A61H 7/00* | (2006.01) |
| *A61L 15/62* | (2006.01) |
| *A61L 15/24* | (2006.01) |
| *A61L 15/26* | (2006.01) |
| *A61L 15/28* | (2006.01) |
| *A61M 1/00* | (2006.01) |

(52) U.S. Cl.
CPC .............. *A61H 7/001* (2013.01); *A61L 15/24* (2013.01); *A61L 15/26* (2013.01); *A61L 15/28* (2013.01); *A61L 15/42* (2013.01); *A61L 15/425* (2013.01); *A61L 15/62* (2013.01); *A61M 1/0088* (2013.01); *A61F 2013/00314* (2013.01); *A61L 2420/08* (2013.01)

(58) Field of Classification Search
CPC ...... A61M 1/0088; A61L 15/28; A61L 15/26; A61L 15/24; A61L 15/62; A61L 15/425; A61L 15/42; A61L 2420/08; A61H 7/001
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A * | 8/1996 | Gross .................. A61M 1/0088 604/313 |
| 5,556,375 A | 9/1996 | Ewall |
| 5,607,388 A | 3/1997 | Ewall |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,143,472 B1 | 3/2012 | Bragd et al. |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 9,655,807 B2 * | 5/2017 | Locke .................... A61H 7/001 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0029675 A1 | 2/2006 | Ginther |
| 2008/0113574 A1 | 5/2008 | Neron et al. |
| 2008/0208147 A1 | 8/2008 | Argenta et al. |

(56) References Cited

U.S. PATENT DOCUMENTS

| | | | |
|---|---|---|---|
| 2010/0160877 A1 | 6/2010 | Kagan et al. | |
| 2011/0092871 A1 | 4/2011 | Fabo et al. | |
| 2014/0163491 A1 | 6/2014 | Schuessler et al. | |
| 2015/0080788 A1 | 3/2015 | Blott et al. | |

FOREIGN PATENT DOCUMENTS

| | | |
|---|---|---|
| AU | 755496 B2 | 12/2002 |
| CA | 2005436 A1 | 6/1990 |
| CN | 101018533 A | 8/2007 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2006014917 A2 | 2/2006 |

OTHER PUBLICATIONS

Louis C. Argenta, MS and Michael J. Morykwas, PHD; Vacuum-Assisted Closure: A New Method for Wound Control and Treatment: Clinical Experience; Annals of Plastic Surgery.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.
Dattilo, Philip P., JR., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp: 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., MD., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A. A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.

(56) References Cited

OTHER PUBLICATIONS

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.Sr. 1988) ("Solovev Abstract").

V.A.C.® Therapy Clinical Guidelines: A Reference Source for Clinicians; Jul. 2007.

\* cited by examiner

TISSUE TREATMENT SYSTEMS AND METHODS HAVING A POROUS SUBSTRATE WITH A COMPRESSED REGION AND AN EXPANDED REGION

CROSS-REFERENCE TO RELATED APPLICATION

This application is a Divisional of U.S. patent application Ser. No. 13/678,459, filed Nov. 15, 2012, which claims priority to U.S. Provisional Patent Application No. 61/561,631 filed Nov. 18, 2011, entitled TISSUE TREATMENT SYSTEMS AND METHODS HAVING A POROUS SUBSTRATE WITH A COMPRESSED REGION AND AN EXPANDED REGION, the disclosure of which is hereby incorporated by reference in its entirety.

BACKGROUND

1. Field

This specification relates generally to tissue treatment systems and more particularly, but without limitation, to a reduced pressure tissue treatment system having a porous substrate with a compressed region and an expanded region.

2. Description of Related Art

Clinical studies and practice have shown that providing a reduced pressure in proximity to a tissue site augments and accelerates the growth of new tissue at the tissue site. The applications of this phenomenon are numerous, but one particular application of reduced pressure involves treating wounds. This treatment (frequently referred to in the medical community as "negative pressure wound therapy," "reduced pressure therapy," or "vacuum therapy") provides a number of benefits, including migration of epithelial and subcutaneous tissues, improved blood flow, and microdeformation of tissue at the wound site. Together these benefits result in increased development of granulation tissue and faster healing times. Typically, reduced pressure is applied by a reduced pressure source to tissue through a porous pad or other manifold device. The porous pad contains cells or pores that are capable of distributing reduced pressure to the tissue and channeling fluids that are drawn from the tissue. The porous pad often is incorporated into a dressing having other components that facilitate treatment.

SUMMARY

The problems presented by existing reduced pressure treatment systems are solved by the systems and methods of the illustrative embodiments described herein. In one illustrative embodiment, a system for treating a tissue site of a patient is provided. The system includes a dressing filler adapted to be positioned at the tissue site. The dressing filler is comprised of a porous substrate having at least one compressed region and at least one expanded region. The compressed region of the porous substrate is held in a compressed state by a first coating capable of dissolving in the presence of a fluid, and the expanded region of the porous substrate is held in an expanded state by a second coating.

In another embodiment, a system for treating a tissue site of a patient includes a dressing filler adapted to be positioned at the tissue site. The dressing filler is comprised of a porous foam having a textured wound-facing surface, the wound-facing surface having at least one compressed region in which the foam is held in a compressed state by a first coating. The wound-facing surface includes at least one relaxed region in which the foam is neither compressed nor expanded but rather is in a relaxed state. The porous foam includes at least one expanded region positioned above the at least one relaxed region. The expanded region is held in an expanded state by a second coating.

In yet another embodiment, a system for treating a tissue site of a patient includes a dressing filler adapted to be positioned at the tissue site. The dressing filler is comprised of a porous substrate having at least one compressed region held in a compressed state by a coating capable of being removed in the presence of a fluid. The system further includes a cover adapted for positioning over the dressing filler to create a sealed space beneath the cover and a reduced pressure source configured for fluid communication with the sealed space.

Other objects, features, and advantages of the illustrative embodiments will become apparent with reference to the drawings and detailed description that follow.

DETAILED DESCRIPTION OF ILLUSTRATIVE EMBODIMENTS

Figure 1A:
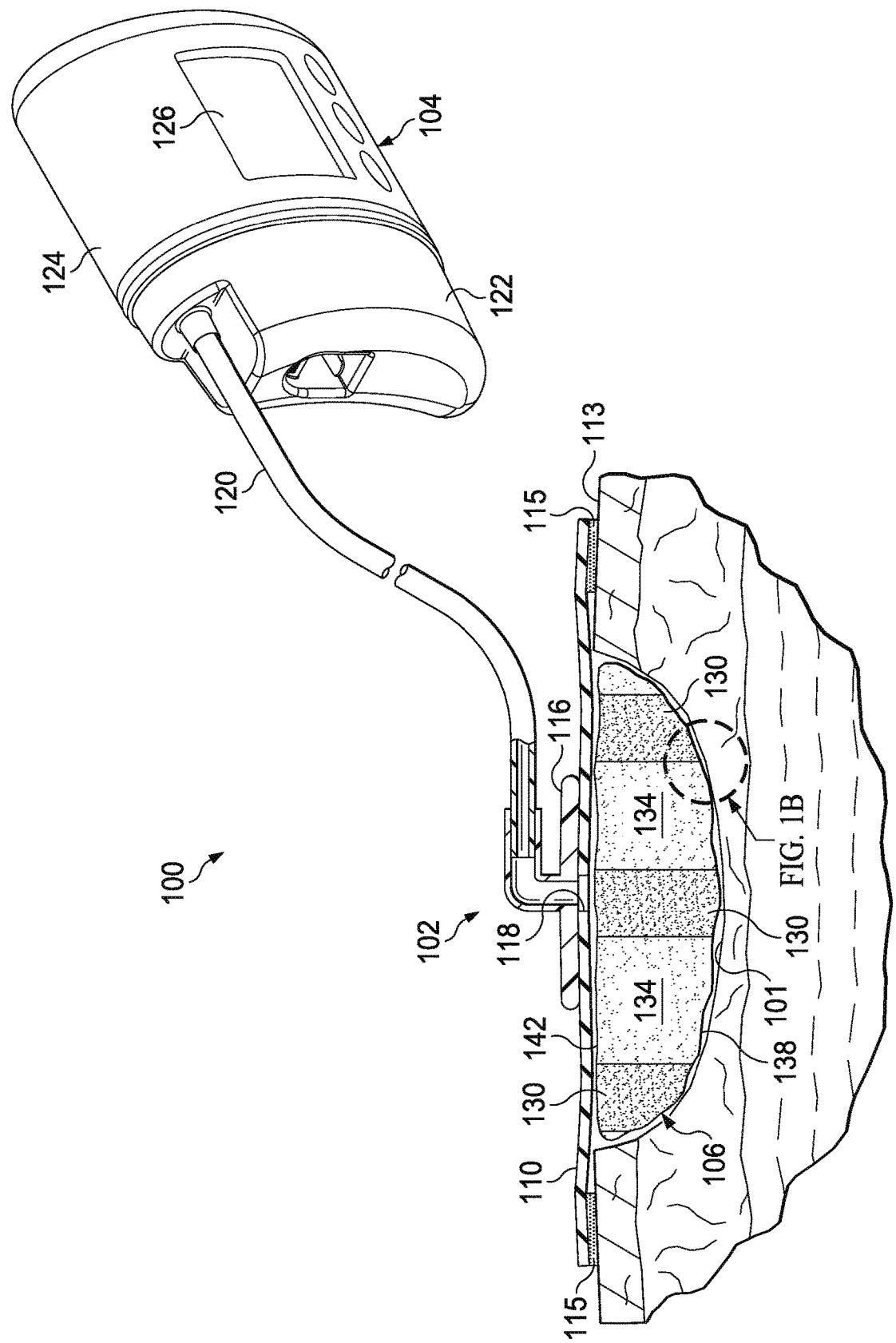
FIGS. 1A and 1B illustrate a partially cross-sectional, perspective view of a tissue treatment system according to an illustrative embodiment, the tissue treatment system having a dressing filler.

In the following detailed description of several illustrative embodiments, reference is made to the accompanying drawings that form a part hereof, and in which is shown by way of illustration specific preferred embodiments in which the subject matter of this specification may be practiced. These embodiments are described in sufficient detail to enable those skilled in the art to practice the disclosed subject matter, and it is understood that other embodiments may be utilized and that logical, structural, mechanical, electrical, and chemical changes may be made without departing from the scope of this specification. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims. Unless otherwise indicated, as used herein, "or" does not require mutual exclusivity.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The tissue treatment systems and methods described herein improve the treatment of a tissue site by providing a porous substrate that is used in conjunction with reduced pressure tissue treatment. The porous substrate includes a wound-facing surface that is capable of contacting the tissue site and creating microstrain at the tissue site. The microstrain is created by the force applied to the tissue site by the wound-facing surface of the porous substrate. When the porous substrate is an open-celled foam, the force is transmitted to the tissue site by the cell walls or struts of the foam. The application of force to the porous substrate produces a force distribution that provides forces to the tissue site at any point that is contacted by the porous substrate. This force distribution therefore results in a particular microstrain distribution, which of course will vary based on the porosity and other characteristics of the porous substrate, as well as how the porous substrate is positioned at the tissue site. Since microstrain at the tissue site assists in the development of new granulation tissue, it is beneficial to vary the distribution of force and microstrain during treatment such that a more even development of granulation tissue is obtained.

Figure 1B:
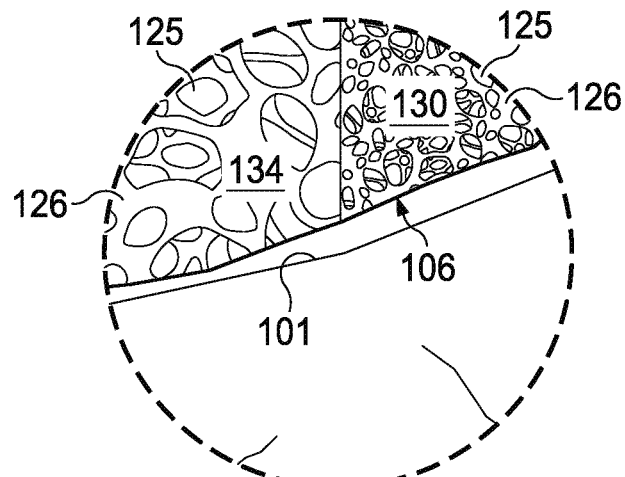

Referring to FIGS. 1A and 1B, an illustrative embodiment of a reduced pressure tissue treatment system 100 for treating a tissue site 101 on a patient includes a dressing 102 placed proximate to the tissue site 101 and a therapy unit 104 fluidly coupled to the dressing 102. As used herein, the term "tissue site" may refer to a wound, such as a wound, or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

The dressing 102 is configured to promote the growth of new tissue at the tissue site 101 and includes a dressing filler 106 positioned adjacent to or, in some embodiments, in contact with the tissue site 101. The dressing 102 may further include a cover 110 or drape positioned over the dressing filler 106 to secure the dressing filler 106 at the tissue site 101 and to seal a space that is located beneath the cover and that is at least partially occupied by the dressing filler 106. In one embodiment, the cover 110 extends beyond a perimeter of the tissue site 101 and is placed either in contact with or otherwise in proximity to a patient's epidermis 113 to create a fluid seal between the cover 110 and the epidermis 113. The cover 110 may include an adhesive 115 or bonding agent to secure the cover 110 to the epidermis 113. In one embodiment, the adhesive 115 may be used to create a seal between the cover 110 and the epidermis 113 to prevent leakage of reduced pressure from the tissue site 101. In another embodiment, a seal layer (not shown) such as, for example, a hydrogel or other material may be disposed between the cover 110 and the epidermis 113 to augment or substitute for the sealing properties of the adhesive 115. As used herein, "fluid seal" means a seal adequate to maintain reduced pressure at a desired site given the particular reduced pressure source involved and the particular treatment desired. In one embodiment, the cover 110 and the bonding characteristics of the cover 110 provide sealing sufficient to prevent leakage greater than 0.5 L/min at 125 mmHg reduced pressure.

The dressing 102 further may include a reduced pressure adapter or interface 116 fluidly coupled to the space beneath the cover 110. In one embodiment, the interface 116 may be positioned adjacent to or coupled to the cover 110 to provide fluid access to the dressing filler 106 and the tissue site 101. The cover 110 includes an aperture 118 for providing fluid access to the interface 116. A conduit 120 fluidly couples the therapy unit 104 and the interface 116. The interface 116 is capable of delivering reduced pressure to the tissue site 101.

In one embodiment, the therapy unit 104 includes a fluid containment member 122 in fluid communication with a reduced pressure source 124. In the embodiment illustrated in FIG. 1, the fluid containment member 122 is a collection canister that includes a chamber for collecting fluids from the tissue site 101. The fluid containment member 122 alternatively could be an absorbent material or any other container, device, or material that is capable of collecting fluid.

The conduit 120 may be a multi-lumen tube that is capable of providing one or more conduits to deliver reduced pressure to the dressing 102 and one or more conduits to sense the amount of pressure at the tissue site 101. Liquids or exudates communicated from the dressing filler 106 through the conduit 120 are removed from the conduit 120 and retained within the collection canister 122.

Referring still to FIG. 1A, the reduced pressure source 124 may be an electrically-driven vacuum pump. In another implementation, the reduced pressure source 124 instead may be a manually-actuated or manually-charged pump that does not require electrical power. In one embodiment, the reduced pressure source 124 may be one or more piezoelectric-actuated micropumps that may be positioned remotely from the dressing 102, or at the dressing beneath or adjacent to the cover 110. The reduced pressure source 124 instead may be any other type of pump, or alternatively a wall suction port or air delivery port such as those available in hospitals and other medical facilities. The reduced pressure source 124 may be housed within or used in conjunction with the therapy unit 104, which may also contain sensors, processing units, alarm indicators, memory, databases, software, display units, and user interfaces 126 that further facilitate the application of reduced pressure treatment to the tissue site 101. In one example, pressure-detection sensors (not shown) may be disposed at or near the reduced pressure source 124. The pressure-detection sensors may receive pressure data from the interface 116 via lumens in the conduit 120 that are dedicated to delivering reduced pressure data to the pressure-detection sensors. The pressure-detection sensors may communicate with a processing unit that monitors and controls the reduced pressure that is delivered by the reduced pressure source 124.

In the embodiment illustrated in FIGS. 1A and 1B, the dressing filler 106 comprises a porous substrate that may be in one embodiment a porous foam. More specifically, the porous substrate may be an open-celled foam such as the open-celled, reticulated polyurethane foam sold under the name GRANUFOAM® by Kinetic Concepts, Inc. of San Antonio, Tex. Alternatively, a non-reticulated foam or a foam comprised of biocompatible materials other than polyurethane may be used. In one embodiment, a bioabsorbable foam or other porous substrate may be employed. Examples of other materials that may be suitable porous foams or porous substrates include those formed from acrylics, acrylates, thermoplastic elastomers (for example, styrene ethylene butene styrene (SEBS) and other block copolymers), polyether block polyamide (PEBAX), silicone elastomers, poly caprolactam, poly lactic acid, and polyolefins, such as polythene and polypropylene. Still other biocompatible materials may be used if capable of being formed or otherwise made into a porous substrate as described herein.

The porous substrate preferably includes a plurality of openings or other flow channels that facilitate movement of fluids and distribution of reduced pressure in the sealed space beneath the cover. In an embodiment employing a foam such as the reticulated, polyurethane foam, the flow channels are provided by openings 125 or cells within the foam. The foam further may include cell walls or struts 126 that form a framework for the openings 125 (see FIG. 1B). The struts 126 press upon the tissue site 101 when a force is applied to the dressing filler 106, thereby creating distribution of forces and microstrain at the tissue site 101 that depends on the local positioning of the struts 126.

Figure 2:
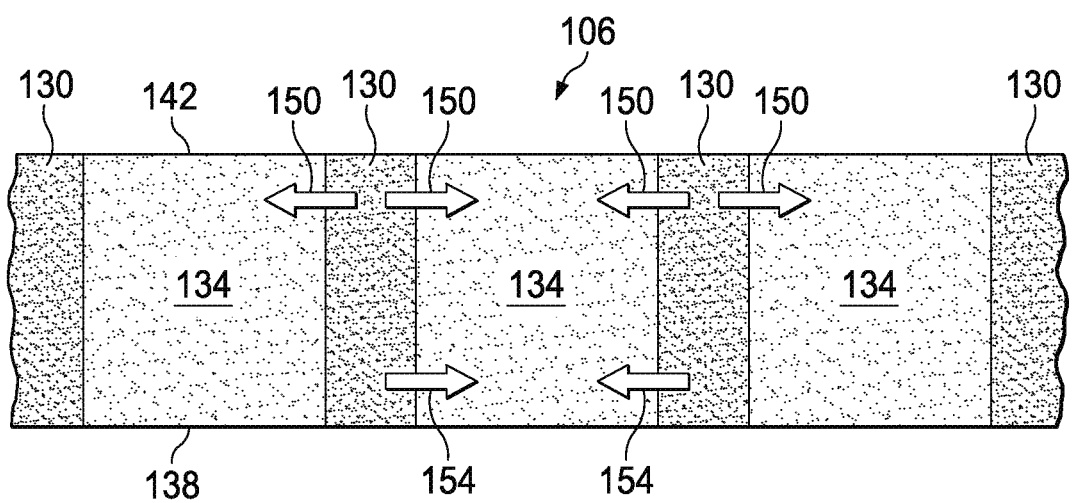
FIG. 2 illustrates a front view of the dressing filler of the tissue treatment system of FIG. 1A, the dressing filler having a plurality of compressed regions in a compressed state and a plurality of expanded regions in an expanded state.
Figure 3:
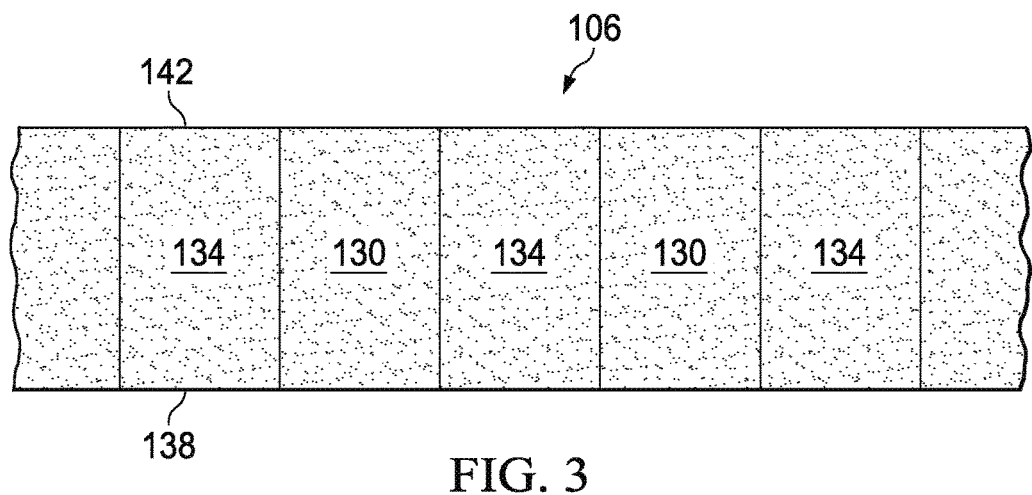
FIG. 3 illustrates a front view of the dressing filler of FIG. 2, both the compressed regions and the expanded regions being illustrated in a relaxed state.

Referring still to FIGS. 1A and 1B, but also to FIGS. 2 and 3, the dressing filler 106 includes a plurality of first, or compressed regions 130 and a plurality of second, or expanded regions 134 arranged in vertically-oriented layers that extend from a wound-facing surface 138 of the porous dressing filler 106 to an opposing surface 142. The compressed regions 130 illustrated in FIGS. 1A, 1B, and 2 are in a compressed state, while the same compressed regions 130 illustrated in FIG. 3 are in a relaxed state. Similarly the expanded regions 134 illustrated in FIGS. 1A, 1B, and 2 are in an expanded state, while the same expanded regions 134 illustrated in FIG. 3 are in a relaxed state. Referring more specifically to FIG. 1B, the effect of compressing or expanding the dressing filler 106 is depicted. When the compressed regions 130 are in the compressed state and the expanded regions 134 are in the expanded state (as depicted in FIG. 1B), the density of struts per unit volume in the compressed regions 130 is greater than the density of struts 126 per unit volume in the expanded regions 134. When the compressed regions 130 and the expanded regions 134 are in the relaxed state (as depicted in FIG. 3), the density of struts per unit volume in the compressed regions 130 is approximately equal to the density of struts 126 per unit volume in the expanded regions 134.

While the phrase "compressed region" has been used to describe certain regions of the dressing filler 106 that are in some cases compressed, the phrase also is capable of describing a region that has assumed a relaxed state from a compressed state. In some situations, due to the compression of the dressing filler 106 during reduced pressure tissue treatment, as is described more fully herein, certain compressed regions may actually experience expansion in certain directions when compared to the original compressed state. Similarly, the "expanded region" is capable of existing in multiple states, at least two of which are the expanded state and the relaxed state. Again, it is conceivable during the application of reduced pressure to the dressing filler 106 that certain expanded regions may undergo some compression beneath the cover 110.

In general, the description of the dressing filler 106 as having a compressed state or an expanded state is meant to describe the forces acting on the foam. When a region of the dressing filler 106 is in the compressed state, the forces acting on the region, which are represented by arrows 150 in FIG. 2, are directed in an outward direction such that the region, if not constrained, would expand in at least one direction. When a region of the dressing filler 106 is in the expanded state, the forces acting on the region, which are represented by arrows 154 in FIG. 2, are directed in an inward direction such that the region, if not constrained, would contract in at least one direction. When a region of the dressing filler 106 is in the relaxed state, no significant forces are acting on the region.

Referring still to FIGS. 1A, 1B, and 2, the compressed regions 130 are held or secured in the compressed state by a first coating. Similarly, the expanded regions 134 are held or secured in the expanded state by a second coating. In one embodiment, the first and second coatings are the same coating. The first and second coatings may be any material that is capable of securing the dressing filler 106 in the compressed state or the expanded state and that is then capable of being removed such that the dressing filler 106 can change to a relaxed state. In one embodiment, the first and second coatings may be capable of dissolving in the presence of a fluid. Dissolvable coatings allow the coating to be removed as exudate from the tissue site 101 enters the dressing filler 106. Alternatively, a liquid such as a saline solution, or any other biocompatible solvent or liquid, may be delivered to the dressing filler 106 when it is desired to remove the first and second coatings. Examples of coatings that may be used include without limitation starches or other sugars, polyvinyl alcohol, polyvinyl pyrrolidone, carboxy methyl cellulose (CMC) and its salts and esters, alginates, gums such as guar and xanthan, or other polymers. Water soluble salts or effervescing mixes (such as tartaric acid and carbonate or bicarbonate salts) may be incorporated into water insoluble polymers. When exposed to water the water soluble salts are leached from the polymer, or in the case of the effervescent mixes gas is released—in both cases creating porosity in the carrier polymer, and weakening it, allowing the physical form of the dressing filler to change. The time period over which the coatings described herein may release will vary depending on the desired treatment regimen. In one embodiment, the coating may be configured to release as quickly as within a few hours (e.g. 4 hours) or as long as a day or more.

The coatings may be positioned on the exterior surfaces of the dressing filler 106 or alternatively may be used to coat both exterior surfaces and the inner passages of the dressing filler 106. In one embodiment, it may be desirable to uniformly coat the dressing filler 106 both externally and internally. Delivery of the coating to the dressing filler 106 may be accomplished by dipping the dressing filler 106 in the coating, or by spraying, brushing, rolling, or otherwise applying the coating. In one embodiment, the coating may be applied to a unitary dressing filler 106 that includes regions that have been compressed and expanded. Alternatively, the coating may be applied to separate pieces of compressed or expanded material that are then assembled to build the dressing filler 106. The attachment of multiple pieces to build the dressing filler 106 may be accomplished by bonding, mechanical fastening, welding, or any other attachment means.

Referring to FIG. 3, as the coating is removed, both compressed and expanded regions are released and move toward a relaxed state as shown in FIG. 3. In the relaxed state, assuming the same type of dressing filler is used in both the compressed and expanded regions, the density of openings and cell struts per unit volume in the compressed regions will be approximately equal to the density of openings and cell struts per unit volume in the expanded regions. By compressing a particular compressed region the same approximate amount as a corresponding expanded region is expanded, the expansion of a compressed region to the relaxed state may be offset by the contraction of an expanded region to the relaxed state. In other words, when a dressing having expanded and compressed regions moves to a relaxed state, the dressing undergoes a net-zero volume change.

As an alternative to the coating, a removable sheath or other covering may be placed around the dressing filler 106 when the various regions have been charged to their appropriate compressed or expanded states. The sheath may be a dissolvable or bioabsorbable substance such as a woven or non-woven fabric, polyvinyl pyrrolidone, carboxy methyl cellulose (CMC) and its salts and esters, alginates, gums such as guar and xanthan, polyvinyl alcohol, polycaprolactam, poly lactic acid and their copolymers or blends, or other polymers or materials. In one embodiment, if a sheath or other covering is used, the sheath may surround the dressing filler 106 completely, or may partially surround a portion of the dressing filler 106. If a dissolvable or bioabsorbable sheath is employed, the particular material used and its thickness may be chosen to provide release based on a desired time period. For example, a sheath that will dissolve within 12 hours may be chosen to provide treatment for up to 12 hours with the regions of dressing filler 106 in the compressed and expanded states. In this particular example, following dissolution of the sheath at or around 12 hours allows the regions of the dressing filler 106 to change to a relaxed state, thereby changing the microstrain profile at the tissue site 101. In another embodiment, the sheath may instead be manually removable from the dressing filler 106 by a care giver or the patient when the change in microstrain profile is desired.

Figure 4:
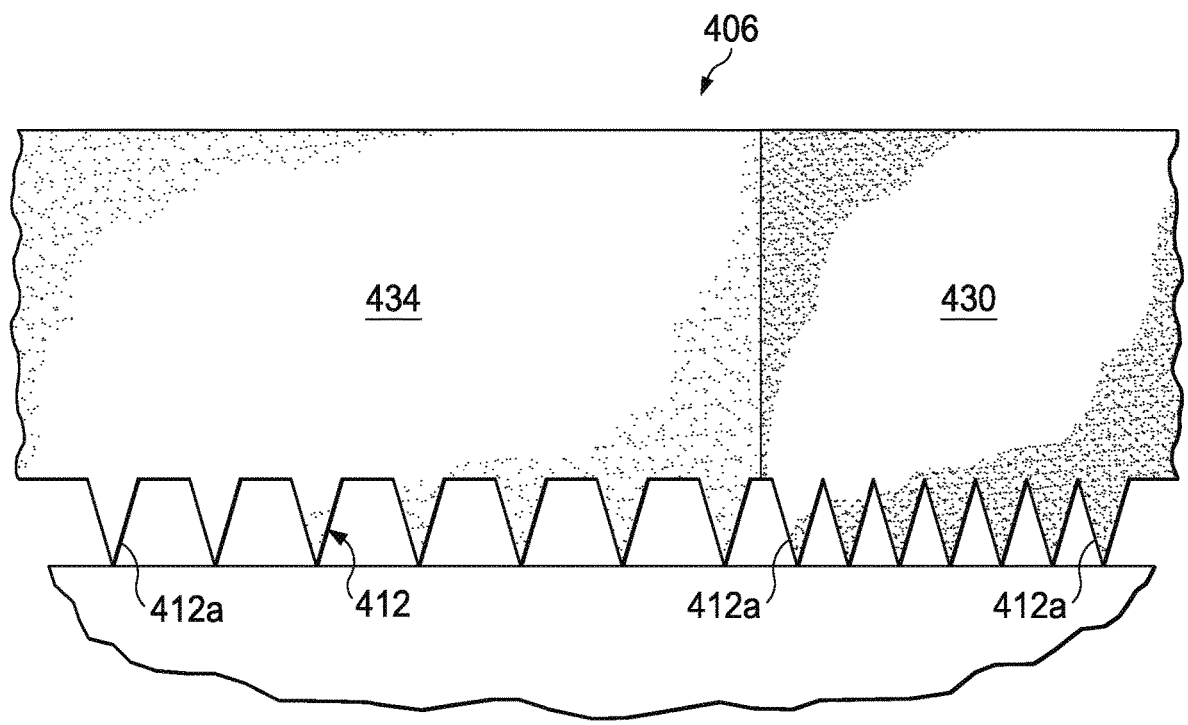
FIG. 4 illustrates a schematic front view of a dressing filler according to an illustrative embodiment, the dressing filler having a compressed region in a compressed state and an expanded region in an expanded state.
Figure 5:
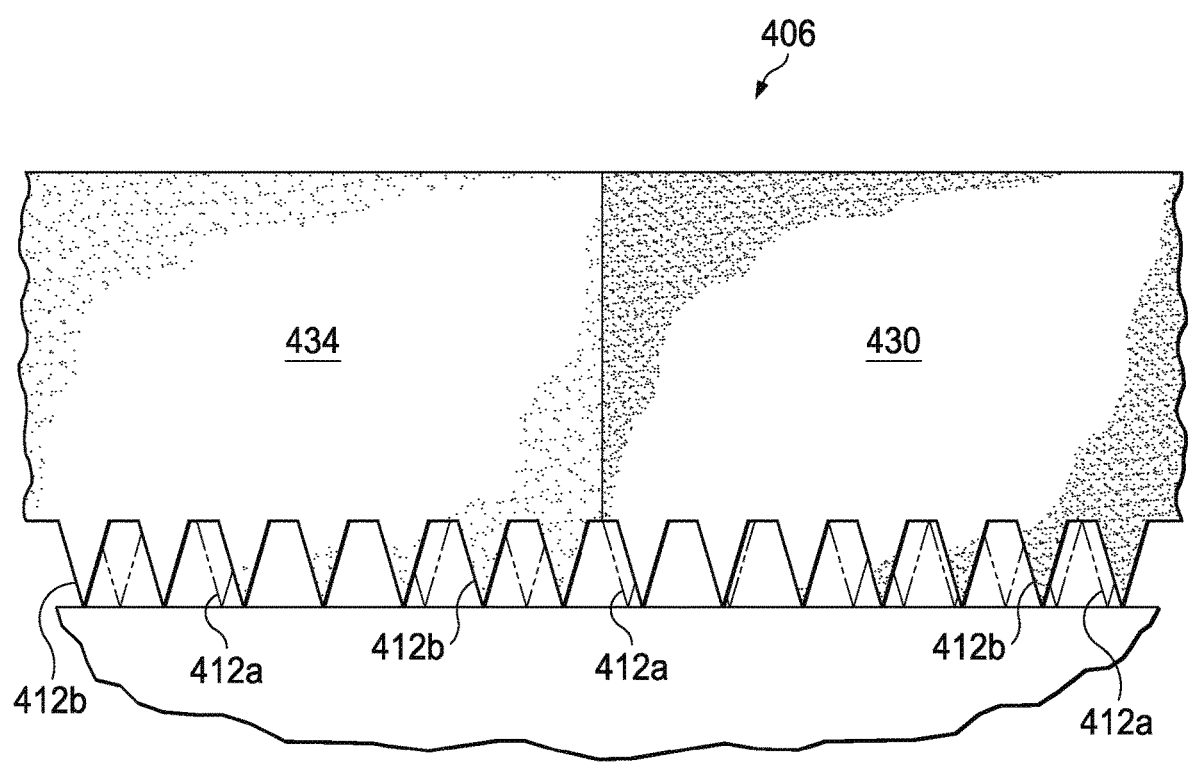
FIG. 5 illustrates a schematic front view of the dressing filler of FIG. 4, the compressed region and the expanded region being illustrated in a relaxed state.

Referring to FIGS. 4 and 5, a dressing filler 406 according to an illustrative embodiment comprises a porous substrate that is similar to the porous substrate described above with reference to FIGS. 1-3. Dressing filler 406 further includes a compressed region 430 and an expanded region 434 similar to those previously described. The dressing filler 406 also includes nodes 412 which may be projections to transmit forces to a tissue site and thus generate microstrain. Nodes 412 may also be representative of the struts of dressing filler 106. Visualization of the nodes 412 illustrated in FIGS. 4 and 5 allows an understanding of how the expansion of the compressed region 430 and the contraction of the expanded region 434 benefit tissue site treatment and wound healing. In FIG. 4, nodes 412 have a first position indicated by nodes 412*a*. As the coating securing the compressed and expanded regions 430, 434 is removed, the compressed region 430 expands and the expanded region 434 contracts, which moves the nodes 412 to a second position indicated by nodes 412*b*. As illustrated in FIG. 5, the repositioning of the nodes 412 during the expansion and contraction of certain regions of the dressing filler 406 allow a spatial redistribution of the point loads applied by the nodes 412 to the tissue site. This in turn creates a different microstrain profile (i.e. the distribution of microstrain) at the tissue site, thereby aiding in the even development of granulation tissue and preventing the adhesion of new tissue growth to the dressing filler 406.

Figure 6:
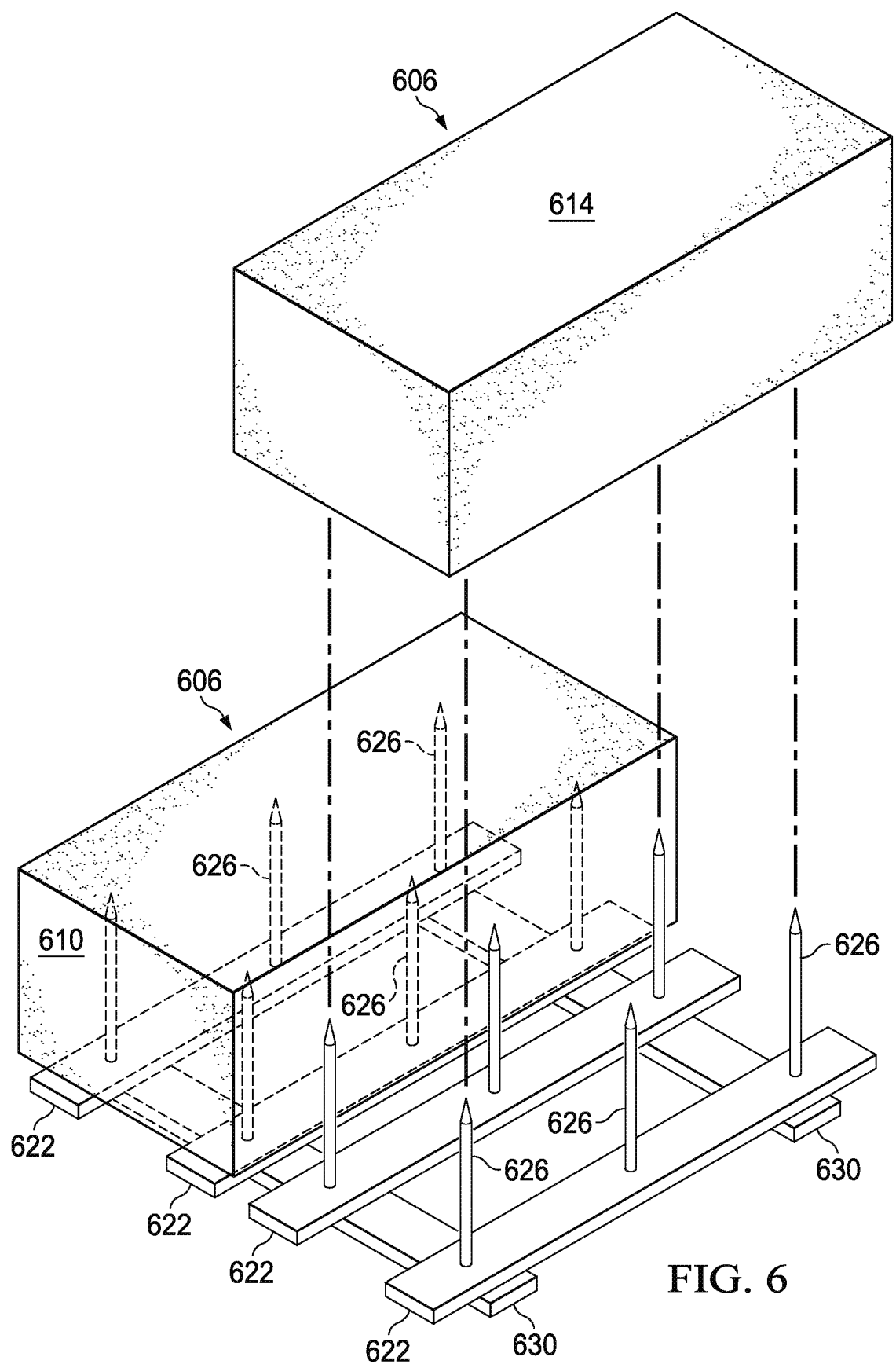
FIG. 6 illustrates a front perspective view of a rack having a plurality of pins for insertion into a porous substrate to form compressed regions or expanded regions within the porous substrate.
Figure 7:
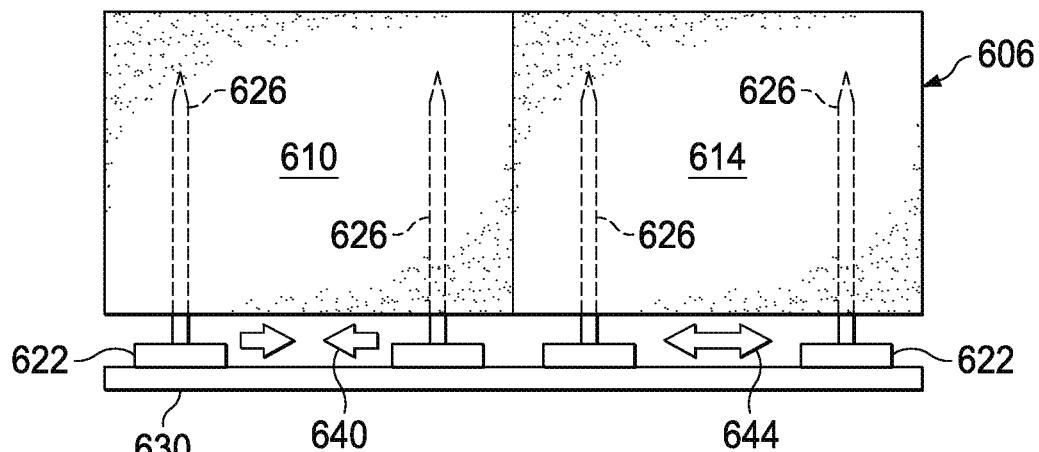
FIG. 7 illustrates the rack of FIG. 6 with the pins of the rack inserted into the porous substrate prior to the compressed region being compressed and prior to the expanded region being expanded.
Figure 8:
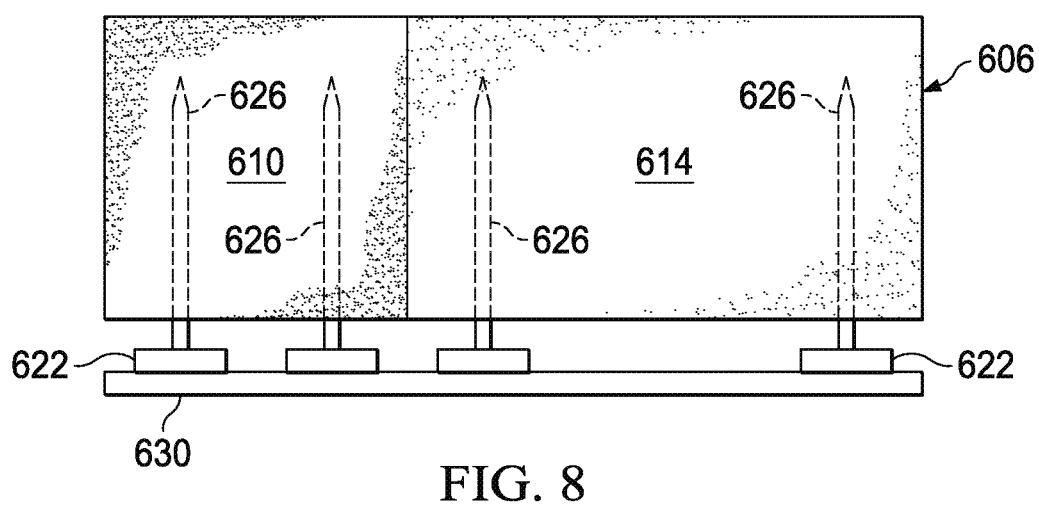
FIG. 8 illustrates the rack of FIG. 6 with the pins of the rack inserted into the porous substrate, the porous substrate being illustrated subsequent to the compressed region being compressed and subsequent to the expanded regions being expanded.

Referring to FIGS. 6-8, a dressing filler 606 similar to dressing fillers 106, 406 is illustrated prior to being placed into a compressed or expanded state. To prepare the dressing filler 606 for use in tissue treatment, the dressing filler 606 is compressed or expanded in sections or regions. In FIG. 6, a first region, or compressed region 610 and a second region, or expanded region 614 are both illustrated in a relaxed state. A plurality of racks 622 each having a plurality of pins 626 are provided to provide the necessary compression or expansion of the dressing filler 606. The racks 622 are slidably positioned on one or more stringers 630 that provide support for the racks 622 and constrain the racks to movements along one axis. In other embodiments, racks may be provided that allow movement, and thus compression or expansion of the dressing filler, along multiple axes.

As more specifically illustrated in FIGS. 6 and 7, the dressing filler is positioned on the pins 626 of the racks 622 such that the pins 626 of at least two of the racks penetrate each region 610, 614. To compress or expand each region 610, 614, the racks 622 are slidably moved along the stringers 630 in the directions illustrated by arrows 640, 644 in FIG. 7. To move the compressed region 610 of the dressing filler 606 to a compressed state, the two racks 622 associated with the compressed region 610 are moved toward one another as indicated by arrows 640. To move the expanded region 614 of the dressing filler 606 to an expanded state, the two racks 622 associated with the expanded region 614 are moved away from one another as indicated by arrows 644. The movement of the racks 622 may be performed manually, or may instead be hydraulically, pneumatically, electrically, or mechanically driven.

Following the movement of the racks 622 in the directions indicated by arrows 640, 644 the compressed region 610 is in the compressed state and the expanded region 614 is in the expanded sate (see FIG. 8). The regions 610, 614 of the dressing filler 606 may be held or secured in the compressed and expanded states by applying a removable coating or sheath to the dressing filler 606 as previously described herein. After the dressing filler 606 has been locked by the coating or sheath, the pins 626 of the racks 622 may be removed from the dressing filler 606.

FIGS. 6-8 provide only one example of how the various regions of the dressing fillers described herein may be compressed or expanded. Other devices that penetrate or contact the regions of the dressing filler may be used to compress or expand the dressing filler. While the examples described above provide a method for compressing and expanding different portions of a unitary piece of foam or porous substrate, the various regions that require compression or expansion may instead by compressed or expanded independently of one another and then joined together to form the dressing filler. For example, in one embodiment, two pieces of a porous foam in a relaxed state may be provided. One of the pieces of porous foam may be compressed and secured in the compressed state. The other piece of porous foam may be expanded and secured in the expanded state. Following the steps of compressing or expanding each piece of foam individually, the two pieces of foam may be adhesively bonded, thermally coupled, mechanically attached, ultrasonically welded, or otherwise connected to form a unitary dressing filler.

Figure 9:
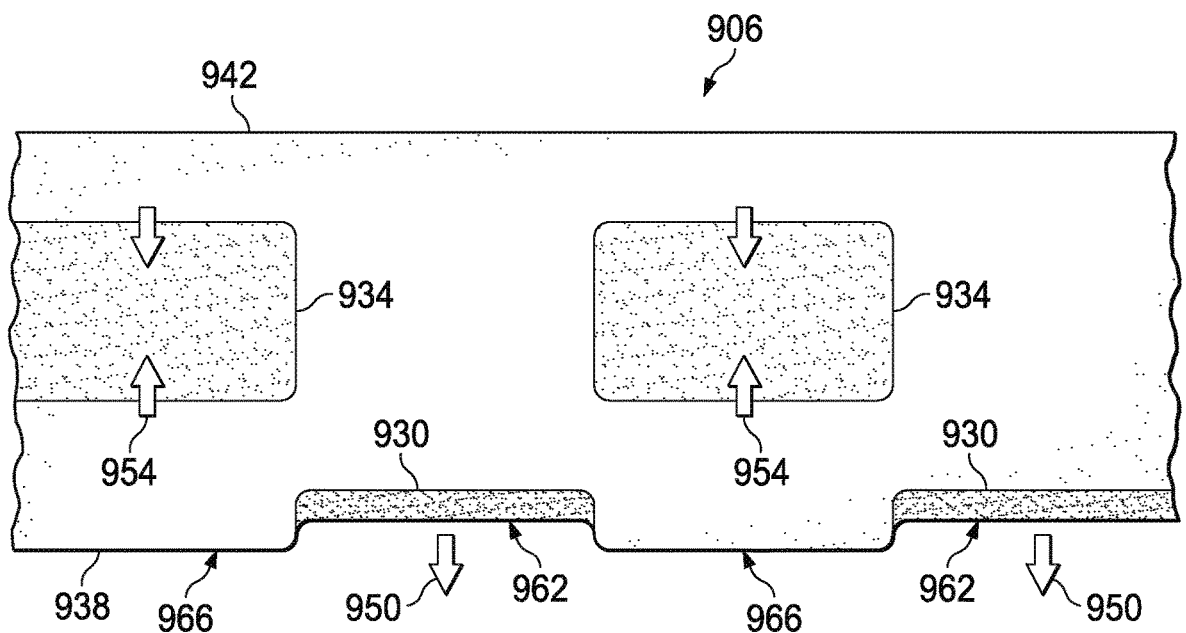
FIG. 9 illustrates a front view of a dressing filler according to an illustrative embodiment, the dressing filler have a plurality of compressed regions in a compressed state and a plurality of expanded regions in an expanded state.
Figure 10:
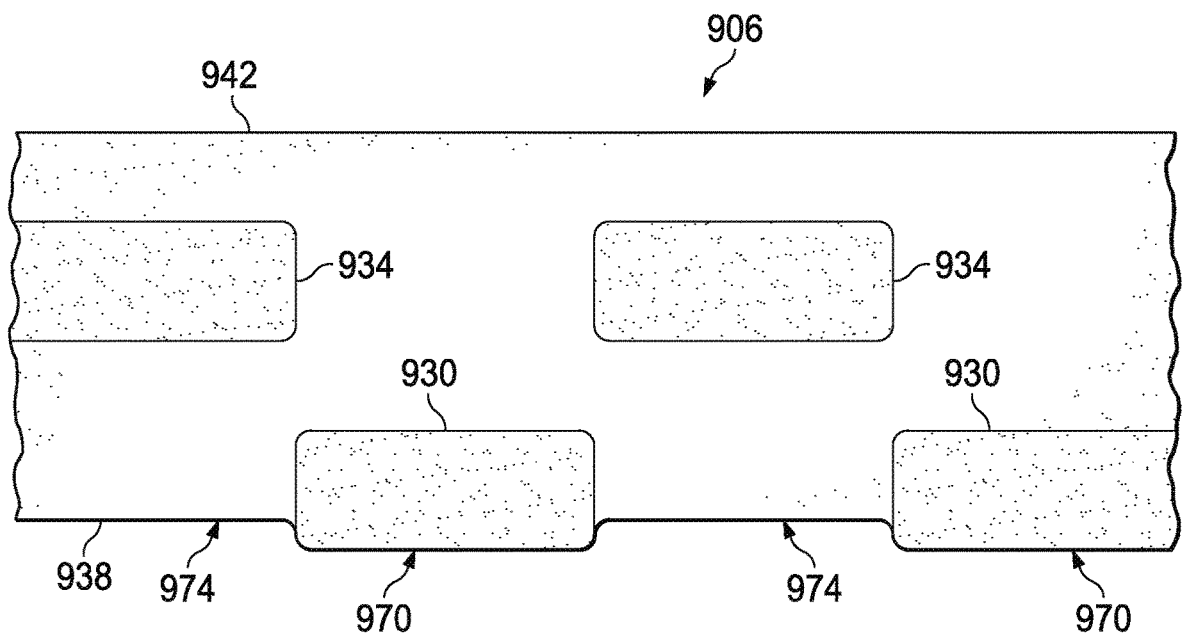
FIG. 10 illustrates a front view of the dressing filler of FIG. 9, the compressed and expanded regions being illustrated in a relaxed state.

Referring to FIGS. 9 and 10, a dressing filler 906 according to an illustrative embodiment is capable of being used with a reduced pressure treatment system similar to reduced pressure treatment system 100 of FIG. 1. The dressing filler 906 comprises a porous substrate that may be in one embodiment a porous foam. More specifically, the porous substrate may be an open-celled foam such as the open-celled, reticulated polyurethane foam sold under the name GRANUFOAM® by Kinetic Concepts, Inc. of San Antonio, Tex. Alternatively, a non-reticulated foam or a foam comprised of biocompatible materials other than polyurethane may be used. In one embodiment, a bioabsorbable foam or other porous substrate may be employed. Examples of other materials that may be suitable porous foams or porous substrates include those formed from acrylics, acrylates, thermoplastic elastomers (for example, styrene ethylene butene styrene (SEBS) and other block copolymers), polyether block polyamide (PEBAX), silicone elastomers, poly caprolactam, poly lactic acid, and polyolefins, such as polythene and polypropylene. Still other biocompatible materials may be used if capable of being formed or otherwise made into a porous substrate as described herein.

The porous substrate preferably includes a plurality of openings or other flow channels that facilitate movement of fluids and distribution of reduced pressure in the sealed space beneath the cover. In an embodiment employing a foam such as the reticulated, polyurethane foam, the flow channels are provided by openings or cells within the foam similar to those described previously with reference to FIGS. 1A and 1B. The foam further may include cell walls or struts that form a framework for the openings as previously described.

The dressing filler 906 includes a plurality of first, or compressed regions 930 and a plurality of second, or expanded regions 934 arranged in horizontally-oriented layers located between a wound-facing surface 938 of the porous dressing filler 906 and an opposing surface 942. The compressed regions 930 illustrated in FIG. 9 are in a compressed state, while the same compressed regions 930 illustrated in FIG. 10 are in a relaxed state. Similarly the expanded regions 934 illustrated in FIG. 9 are in an expanded state, while the same expanded regions 934 illustrated in FIG. 10 are in a relaxed state.

The forces acting on the compressed region 930 in the compressed state are represented by arrows 950 in FIG. 9. These particular forces are directed in an outward direction such that the compressed region 930 in the compressed state, if not constrained, would expand in at least one direction. The forces acting on the expanded region 934 in the expanded state are represented by arrows 954 in FIG. 9. These forces are directed in an inward direction such that the expanded region 934 in the expanded state, if not constrained, would contract in at least one direction. When the compressed regions 930 or the expanded regions 934 of the dressing filler 906 are in the relaxed state (see FIG. 10), no significant forces are acting on the regions.

Referring still to FIG. 9, the compressed regions 930 are held or secured in the compressed state by a first coating. Similarly, the expanded regions 934 are held or secured in the expanded state by a second coating. In one embodiment, the first and second coatings are the same coating. The first and second coatings may be any material that is capable of securing the dressing filler 906 in the compressed state or the expanded state and that is then capable of being removed such that the dressing filler 906 may change to a relaxed state. In one embodiment, the first and second coatings may be capable of dissolving in the presence of a fluid. Dissolvable coatings allow the coating to be removed as exudate from a tissue site enters the dressing filler 906. Alternatively, a liquid such as a saline solution, or any other biocompatible solvent or liquid, may be delivered to the dressing filler 906 when it is desired to remove the first and second coatings. Examples of coatings that may be used include without limitation starches or other sugars, polyvinyl alcohol, polyvinyl pyrrolidone, carboxy methyl cellulose (CMC) and its salts and esters, alginates, gums such as guar and xanthan, or other polymers. Water soluble salts or effervescing mixes (such as tartaric acid and carbonate or bicarbonate salts) may be incorporated into water insoluble polymers. When exposed to water the water soluble salts are leached from the polymer, or in the case of the effervescent mixes gas is released—in both cases creating porosity in the carrier polymer, and weakening it, allowing the physical form of the dressing filler to change. The time period over which the coatings described herein may release will vary depending on the desired treatment regimen. In one embodiment, the coating may be configured to release as quickly as within a few hours (e.g. 4 hours) or as long as a day or more.

The coatings may be positioned on the exterior surfaces of the dressing filler 906 or alternatively may be used to coat both exterior surfaces and the inner passages of the dressing filler 906. In one embodiment, it may be desirable to uniformly coat the dressing filler 906 both externally and internally. Delivery of the coating to the dressing filler 906 may be accomplished by dipping the dressing filler 906 within the coating, or by spraying, brushing, rolling, or otherwise applying the coating. In one embodiment, the coating may be applied to a unitary dressing filler 906 that includes regions that have been compressed and expanded. Alternatively, the coating may be applied to separate pieces of compressed or expanded material that is then assembled to build the dressing filler 906. The attachment of multiple pieces to build the dressing filler 906 may be accomplished by bonding, mechanical fastening, welding, or any other attachment means.

Prior to removal of the coating, the wound-facing surface 938 of the dressing filler 906 is irregular or non-planar, with indentations 962 created by the compression of the compressed regions 930. The wound-facing surface 938 further includes protrusions 966 created by the expansion of the expanded regions 934. The location of the indentations 962 and protrusions 966 along the wound-facing surface may form a regular grid-type or other pattern, or may instead be more random in nature. While the compressed regions 930 are located adjacent to and incorporate the wound-facing surface 938, the compressed regions 930 could instead be spaced apart from the wound-facing surface 938 and located closer to opposing surface 942. Similarly, while the expanded regions 934 are spaced apart from the wound-facing surface 938 and are located closer to the opposing surface 942, the expanded regions 934 could instead be positioned adjacent to and may even incorporate the wound-facing surface 938.

Referring to FIG. 10, as the coating is removed, both the compressed and expanded regions are released and move toward a relaxed state as shown in FIG. 10. In the relaxed state, assuming the same type of dressing filler is used in both the compressed and expanded regions, the density of openings and cell struts per unit volume in the compressed regions will be approximately equal to the density of openings and cell struts per unit volume in the expanded regions. The height of the expanded regions 934 typically decreases as the expanded regions 934 move to the relaxed state, while the height of the compressed regions 930 typically increases as the compressed regions 930 move to the relaxed state. The change in height of the compressed and expanded regions results in a change in the profile of the wound-facing surface 938. While the compressed regions 930 had previously been associated with indentations 962 (see FIG. 9), the expansion of the compressed regions 930 to the relaxed state results in the formation of protrusions 970 (see FIG. 10). The expanded regions 934, which had previously been associated with protrusions 966 (see FIG. 9), contract to the relaxed state such that indentations 974 are formed (see FIG. 10). This reversal of protrusions and indentations on the wound-facing surface 938 changes the interface of the dressing filler 906 with a tissue site and therefore is capable of changing the distribution of loads and microstrain at the tissue site during treatment.

As an alternative to the coating, a removable sheath or other covering may be placed around the dressing filler 906 when the various regions have been charged to their respective compressed or expanded states. The sheath may be a dissolvable or bioabsorbable substance such as a woven or non-woven fabric, polyvinyl pyrrolidone, carboxy methyl cellulose (CMC) and its salts and esters, alginates, gums such as guar and xanthan, polyvinyl alcohol, polycaprolactam, poly lactic acid and their copolymers or blends, or other polymers or materials. In one embodiment, if a sheath or other covering is used, the sheath may surround the dressing filler 906 completely, or may partially surround a portion of the dressing filler 906. If a dissolvable or bioabsorbable sheath is employed, the particular material used and its thickness may be chosen to provide release based on a desired time period. In another embodiment, the sheath may instead be manually removable from the dressing filler 906 by a care giver or the patient when the change in microstrain profile is desired.

Figure 11:
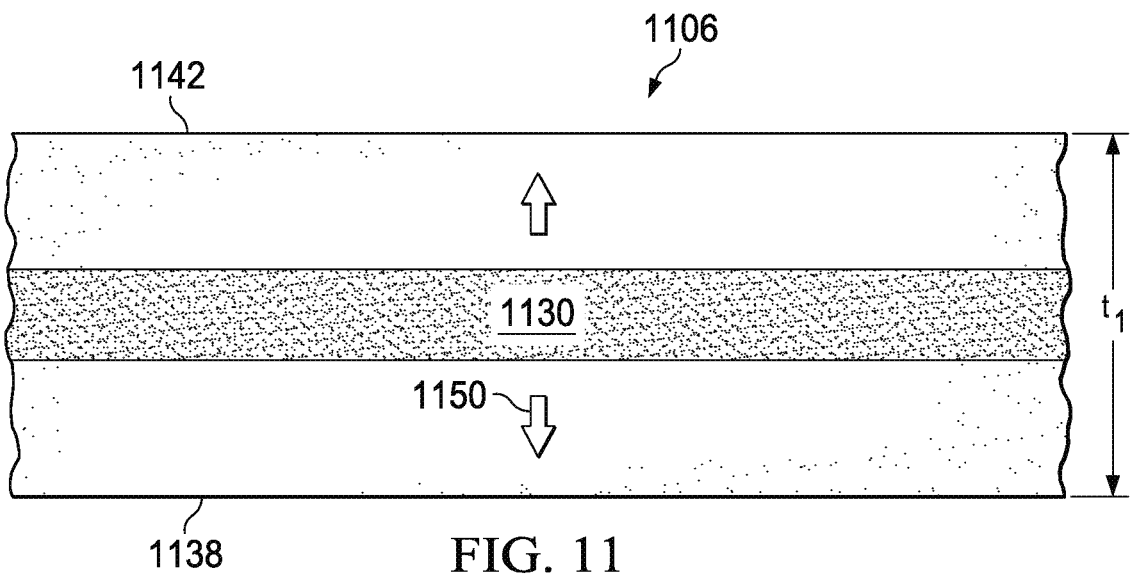
FIG. 11 illustrates a front view of a dressing filler according to an illustrative embodiment, the dressing filler have a compressed region in a compressed state.
Figure 12:
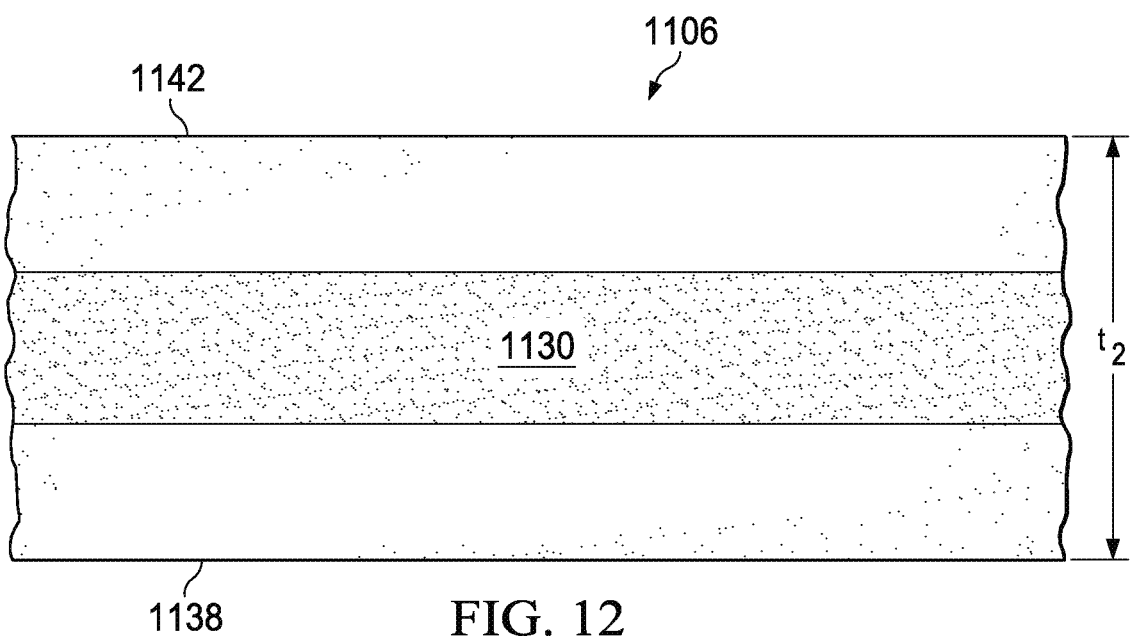
FIG. 12 illustrates a front view of the dressing filler of FIG. 11, the compressed region being illustrated in a relaxed state.

Referring to FIGS. 11 and 12, a dressing filler 1106 according to an illustrative embodiment is capable of being used with a reduced pressure treatment system similar to reduced pressure treatment system 100 of FIG. 1. The dressing filler 1106 comprises a porous substrate that may be in one embodiment a porous foam. More specifically, the porous substrate may be an open-celled foam such as the open-celled, reticulated polyurethane foam sold under the name GRANUFOAM® by Kinetic Concepts, Inc. of San Antonio, Tex. Alternatively, a non-reticulated foam or a foam comprised of biocompatible materials other than polyurethane may be used. In one embodiment, a bioabsorbable foam or other porous substrate may be employed. Examples of other materials that may be suitable porous foams or porous substrates include those formed from acrylics, acrylates, thermoplastic elastomers (for example, styrene ethylene butene styrene (SEBS) and other block copolymers), polyether block polyamide (PEBAX), silicone elastomers, poly caprolactam, poly lactic acid, and polyolefins, such as polythene and polypropylene. Still other biocompatible materials may be used if capable of being formed or otherwise made into a porous substrate as described herein.

The porous substrate preferably includes a plurality of openings or other flow channels that facilitate movement of fluids and distribution of reduced pressure in the sealed space beneath the cover. In an embodiment employing a foam such as the reticulated, polyurethane foam, the flow channels are provided by openings or cells within the foam similar to those described previously with reference to FIGS. 1A and 1B. The foam further may include cell walls or struts that form a framework for the openings as previously described.

The dressing filler 1106 includes one or more compressed regions 1130 arranged in horizontally-oriented layers located between a wound-facing surface 1138 of the porous dressing filler 1106 and an opposing surface 1142. The compressed region 1130 illustrated in FIG. 11 is in a compressed state, while the same compressed region 1130 illustrated in FIG. 12 is in a relaxed state. The forces acting on the compressed region 1130 in the compressed state are represented by arrows 1150 in FIG. 11. These particular forces are directed in an outward direction such that the compressed region 1130 in the compressed state, if not constrained, would expand in at least one direction. When the compressed region 1130 of the dressing filler 1106 is in the relaxed state (see FIG. 12), no significant forces act upon the compressed region 1130.

Referring still to FIG. 11, the compressed region 1130 is held or secured in the compressed state by a coating. The coating may be any material that is capable of securing the dressing filler 1106 in the compressed state and that is then capable of being removed such that the dressing filler 1106 may change to a relaxed state. In one embodiment, the coating may be capable of dissolving in the presence of a fluid. Dissolvable coatings allow the coating to be removed as exudate from a tissue site enters the dressing filler 1106. Alternatively, a liquid such as a saline solution, or any other biocompatible solvent or liquid, may be delivered to the dressing filler 1106 when it is desired to remove the coating. Examples of coatings that may be used include without limitation starches or other sugars, polyvinyl alcohol, polyvinyl pyrrolidone, carboxy methyl cellulose (CMC) and its salts and esters, alginates, gums such as guar and xanthan, or other polymers. Water soluble salts or effervescing mixes (such as tartaric acid and carbonate or bicarbonate salts) may be incorporated into water insoluble polymers. When exposed to water the water soluble salts are leached from the polymer, or in the case of the effervescent mixes gas is released—in both cases creating porosity in the carrier polymer, and weakening it, allowing the physical form of the dressing filler to change. The time period over which the coatings described herein may release will vary depending on the desired treatment regimen. In one embodiment, the coating may be configured to release as quickly as within a few hours (e.g. 4 hours) or as long as a day or more.

The coatings may be positioned on the exterior surfaces of the dressing filler 1106 or alternatively may be used to coat both exterior surfaces and the inner passages of the dressing filler 1106. In one embodiment, it may be desirable to uniformly coat the dressing filler 1106 both externally and internally. Delivery of the coating to the dressing filler 1106 may be accomplished by dipping the dressing filler 1106 within the coating, or by spraying, brushing, rolling, or otherwise applying the coating. In one embodiment, the coating may be applied to a unitary dressing filler 1106 that includes regions that have been compressed. Alternatively, the coating may be applied to separate pieces of compressed material that is then assembled to build the dressing filler 1106. The attachment of multiple pieces to build the dressing filler 1106 may be accomplished by bonding, mechanical fastening, welding, or any other attachment means.

Referring to FIG. 12, as the coating is removed, the compressed region is released and moves toward a relaxed state as shown in FIG. 12. In the relaxed state, assuming the same type of dressing filler is used in the compressed and the rest of the dressing filler 1106, the density of openings and cell struts per unit volume in the compressed regions will be approximately equal to the density of openings and cell struts per unit volume in the remainder of the dressing filler 1106. The height of the compressed region 1130 typically increases as the compressed region 1130 moves to the relaxed state.

Unlike dressing filler 106 in which there may be zero net volume gain, the presence of the compressed region 1130 with no expanded region in the dressing filler 1106 results in a positive net volume gain when the compressed region 1130 moves to the relaxed state. When the dressing filler 1106 is sealed beneath a cover similar to cover 110 during tissue treatment, the change in height of the compressed region, and thus the increase in volume of the dressing filler 1106, results in an increase in the force applied to the tissue site. This increase in force could be used to ensure patient comfort by gradually increasing the force applied to the tissue site as treatment begins. Alternatively, the increase in force may allow a wider range of treatment regimens that promote new tissue growth.

As an alternative to the coating, a removable sheath or other covering may be placed around the dressing filler 1106 when the compressed region has been charged to its compressed state. The sheath may be a dissolvable or bioabsorbable substance such as a woven or non-woven fabric, polyvinyl pyrrolidone, carboxy methyl cellulose (CMC) and its salts and esters, alginates, gums such as guar and xanthan, polyvinyl alcohol, polycaprolactam, poly lactic acid and their copolymers or blends, or other polymers or materials. In one embodiment, if a sheath or other covering is used, the sheath may surround the dressing filler 1106 completely, or may partially surround a portion of the dressing filler 1106. If a dissolvable or bioabsorbable sheath is employed, the particular material used and its thickness may be chosen to provide release based on a desired time period. In another embodiment, the sheath may instead be manually removed from the dressing filler 1106 by a care giver or the patient when the change in treatment force is desired.

Each of the dressing fillers 106, 406, 606, 906, 1106 described herein may be used with the reduced pressure treatment system 100 of FIG. 1 or similar reduced pressure treatment systems to encourage new tissue growth at a tissue site. During reduced pressure treatment, as reduced pressure is applied to the sealed space beneath the cover, the cover presses on the dressing filler, thereby urging the dressing filler toward the tissue site. Some of the structural components (e.g. struts 126 or nodes 412) of the dressing filler contact the tissue site, and these structural components provide point loads to the tissue site, thereby creating a particular distribution of microstrain across the tissue site. When the coating associated with the dressing filler is removed, the various regions of the dressing filler that have been expanded or compressed change state, which prompts movement of the dressing filler and the associated structural components. In the case of dressing fillers 106, 406, 606, and 906, this movement causes a spatial redistribution of the point loads applied by the structural components to the tissue site. This in turn creates a different microstrain profile (i.e. the distribution of microstrain) at the tissue site and helps prevent adhesion of new tissue growth to the dressing filler. In the case of dressing fillers 906, 1106, the movement of the dressing filler is capable of changing the magnitude of the point loads applied to the tissue site. This also creates a different microstrain profile which is beneficial to wound healing.

The systems and methods described herein allow modification of the microstrain experienced by a tissue site without changing the dressing at the tissue site. In some cases, the microstrain modification involves simply a redistribution of the microstrain profile, while in other cases, the amplitude of the microstrain may be increased or decreased. The dressings described herein each incorporate nodes, struts, or other strain-inducing structures that include at least one compressed region that is selectively held in a compressed state or expanded region that is selectively held in an expanded state. When released, the compressed or expanded regions move to a relaxed state, which changes the distribution or amount of microstrain applied to the tissue site. Each of the dressings described herein is therefore believed to improve the treatment of a tissue site using reduced pressure tissue treatment, since changing the microstrain profile during reduced pressure treatment will result in more even formation of granulation tissue and will prevent adhesion of new tissue to the dressing.

While many of the systems described herein have been illustrated in use with tissue sites or wounds that are at or near the epidermis of a patient, the systems and methods may similarly be used to treat subcutaneous tissue sites, tunnel wounds, or other undermined areas of tissue.

While a number of discrete embodiments have been described, aspects of each embodiment may not be specific to only that embodiment and it is specifically contemplated that features of embodiments may be combined with features of other embodiments. While the subject matter of this specification is shown in only a few of its forms, it is susceptible to various changes and modifications without departing from the scope thereof.

Variations on the embodiments described herein comprising both a compressed and expanded region may be provided utilizing only an expanded or only a compressed region. For example, the embodiment of FIG. 1 may be modified to utilize only vertical compressed or expanded regions, but not regions of both types.

Where reference is made to a dimension, part, or region being horizontal this is with reference to a plane substantially parallel with the wound-facing surface of the dressing. Similarly, vertical is referenced to this plane and so describes a plane running substantially perpendicular to the wound-facing surface. Where reference is made to one part being 'above' or 'below' another part, this is made with reference to the wound-facing surface being the 'bottom' of the dressing.

The coatings securing the compressed and expanded regions may be different such that the first and second coatings may be removed at a different time. For example, the coatings may be of different materials, or configured to dissolve over differing periods of time.

We claim:

1. A system for treating a tissue site, the system comprising:
   a dressing filler adapted to be positioned at the tissue site, the dressing filler comprising a porous foam having a textured wound-facing surface,
   the textured wound-facing surface including at least one compressed region in which the porous foam is held away from a relaxed state and in a compressed state by a first coating;
   the textured wound-facing surface further including a first indentation associated with the at least one compressed region when the at least one compressed region is in the compressed state; and
   wherein a height of the at least one compressed region increases as the at least one compressed region moves from the compressed state to the relaxed state.

2. The system of claim 1, further comprising a cover configured to be positioned adjacent the dressing filler to create a sealed space beneath the cover.

3. The system of claim 1, further comprising a reduced pressure source configured to be in fluid communication with the dressing filler.

4. The system of claim 1, wherein the porous foam includes at least one expanded region in which the porous foam is held away from a relaxed state and in an expanded state by a second coating, the textured wound facing-surface further including a first protrusion associated with the at least one expanded region when the at least one expanded region is in the expanded state.

5. The system of claim 4, wherein the at least one compressed region is configured to expand to the relaxed state upon removal of the first coating, wherein a profile of the textured wound-facing surface is configured to change such that the first indentation associated with the at least one compressed region in the compressed state transforms to a second protrusion as the at least one compressed region expands to the relaxed state.

6. The system of claim 4, wherein the at least one expanded region is configured to contract to the relaxed state upon removal of the second coating, wherein a profile of the textured wound-facing surface is configured to change such that the first protrusion associated with the at least one expanded region in the expanded state transforms to a second indentation as the at least one expanded region contracts to the relaxed state.

7. The system of claim 1, wherein the porous foam is an open-cell, reticulated foam.

8. The system of claim 1, wherein the porous foam is a polyurethane foam.

9. The system of claim 4, wherein the porous foam includes an equal number of the at least one compressed region and the at least one expanded region.

10. The system of claim 4, wherein the first coating and the second coating are configured to be removed in a presence of exudate from the tissue site.

11. The system of claim 4, wherein at least one of the first coating or the second coating comprises a starch.

12. The system of claim 4, wherein at least one of the first coating or the second coating comprises polyvinyl alcohol.

13. The system of claim 4, wherein at least one of the first coating or the second coating comprises a polymer.

14. The system of claim 4, wherein the first coating and the second coating are the same coating.

15. The system of claim 4, wherein the porous foam includes a plurality of pores, and wherein the pores of the at least one compressed region are smaller than the pores of the at least one expanded region.

16. The system of claim 4, wherein the at least one compressed region is arranged as a first horizontal layer and is positioned on the textured wound-facing surface, and wherein the at least one expanded region is arranged as a second horizontal layer and is separated from the textured wound-facing surface.

17. A system for treating a tissue site, the system comprising:
   a dressing filler configured to be positioned at the tissue site, the dressing filler comprising a porous substrate having at least one expanded region;
   wherein the at least one expanded region is held away from a relaxed state and in an expanded state by a coating, and wherein the coating is configured to be removed in a presence of a fluid; and
   wherein at least one of a height or a width of the at least one expanded region decreases as the at least one expanded region moves from the expanded state to the relaxed state.

18. The system of claim 17, wherein the at least one expanded region is configured to contract to the relaxed state upon removal of the coating.

19. The system of claim 17, wherein the coating is a second coating, wherein the porous substrate comprises at least one compressed region, wherein the at least one compressed region is held away from a relaxed state and in a compressed state by a first coating, and wherein the first coating is configured to be removed in a presence of a fluid.

20. The system of claim 19, wherein as the first coating and the second coating are removed, an expansion of the at least one compressed region and a contraction of the at least one expanded region occurs as the at least one compressed region and the at least one expanded region each return to the relaxed state to produce a net zero change in a volume of the porous substrate.

21. The system of claim 17, wherein the porous substrate is an open-cell, reticulated foam.

22. The system of claim 19, wherein the porous substrate includes an equal number of the at least one compressed region and the at least one expanded region.

23. The system of claim 17, wherein the fluid comprises exudate from the tissue site.

24. The system of claim 19, wherein at least one of the first coating or the second coating comprises at least one of a starch, polyvinyl alcohol, or a polymer.

25. The system of claim 19, wherein the first coating and the second coating comprise a same coating.

26. The system of claim 19, wherein the porous substrate includes a plurality of pores, and wherein the pores of the at least one compressed region are smaller than the pores of the at least one expanded region.

27. The system of claim 19, wherein the at least one compressed region is arranged in a vertical layer such that the at least one compressed region is configured to extend from a wound-facing surface of the porous substrate to an opposing surface of the porous substrate, and wherein the at least one expanded region is arranged in a vertical layer such that the at least one expanded region extends from the wound-facing surface to the opposing surface of the porous substrate.

28. The system of claim 19, wherein a surface of at least one of the at least one compressed region or the at least one expanded region is arranged in a wound-facing surface of the porous substrate.

29. The system of claim 19, wherein at least one of the at least one compressed region or the at least one expanded region is within the dressing filler and away from a wound-facing surface of the porous substrate.

30. The system of claim 17, wherein a wound-facing surface of the dressing filler comprises a non-planar surface.

31. The system of claim 17, wherein a wound-facing surface of the dressing filler comprises protrusions.

32. A dressing filler, comprising:
a porous substrate having at least one expanded region, the at least one expanded region held away from a relaxed state and in an expanded state by a coating adapted to dissolve in a presence of exudate from a tissue site; and
wherein at least one of a height or a width of the at least one expanded region decreases as the at least one expanded region moves from the expanded state to the relaxed state.

33. The dressing filler of claim 32, wherein the at least one expanded region is adapted to contract to the relaxed state upon dissolution of the coating.

34. The dressing filler of claim 32, wherein the coating is a second coating, the porous substrate further comprising at least one compressed region, the at least one compressed region held away from a relaxed state and in a compressed state by a first coating adapted to dissolve in the presence of the exudate, wherein the at least one compressed region is adapted to expand to the relaxed state upon dissolution of the first coating.

* * * * *

UNITED STATES PATENT AND TRADEMARK OFFICE
CERTIFICATE OF CORRECTION

PATENT NO. : 10,716,711 B2
APPLICATION NO. : 15/488156
DATED : July 21, 2020
INVENTOR(S) : Christopher Brian Locke et al.

It is certified that error appears in the above-identified patent and that said Letters Patent is hereby corrected as shown below:

On the Title Page

<u>On Page 2, Column 1, item (56) Under (Other Publications)</u>
Line 1, delete "MS" and insert -- MD --, therefor.
Line 10, delete "Philidelphia," and insert -- Philadelphia, --, therefor.

<u>On Page 2, Column 2, item (56) Under (Other Publications)</u>
Line 71, delete "Hypermia" and insert -- Hyperemia --, therefor.

In the Specification

<u>Column 8</u>
Line 63, delete "sate" and insert -- state --, therefor.

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*